United States Patent [19]
Bouali et al.

[11] Patent Number: 6,011,026
[45] Date of Patent: *Jan. 4, 2000

[54] METHOD OF TREATING MENOPAUSE OR PERIMENOPAUSE

[75] Inventors: Yamina Bouali, Villejuif; Daniel Philibert, La Varenne Saint Hilaire; Francois Nique, Le Perreux Sur Marne; Jean-Georges Teutsch, Pantin; Patrick Van De Velde, Paris, all of France

[73] Assignee: Hoeschst Marion Roussel, France

[ * ] Notice: This patent is subject to a terminal disclaimer.

[21] Appl. No.: 09/249,416

[22] Filed: Feb. 12, 1999

Related U.S. Application Data

[63] Continuation of application No. 08/993,848, Dec. 18, 1997.

[30] Foreign Application Priority Data

Dec. 23, 1996 [FR] France ................................. 96-15828

[51] Int. Cl.⁷ ........................ A61K 31/56; A61K 31/585
[52] U.S. Cl. .......................... 514/178; 514/175; 514/182
[58] Field of Search .................................. 514/182, 178, 514/175

Primary Examiner—T. J. Criares
Attorney, Agent, or Firm—Bierman, Muserlian and Lucas

[57] ABSTRACT

A method of treating menopause or perimenopause without estrogenic activity at the uterine level in women comprising administering to women an amount of a steroid of the formula

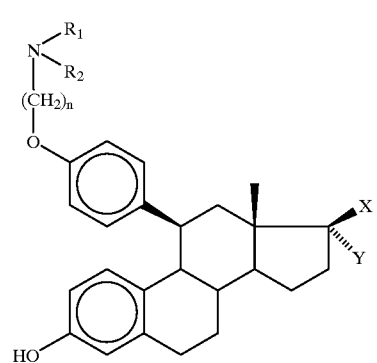

wherein the substituents are defined as in the specification sufficient to treat menopause or perimenopause symptoms without estrogenic activity at the uterine level.

7 Claims, No Drawings

METHOD OF TREATING MENOPAUSE OR PERIMENOPAUSE

PRIOR APPLICATION

This application is a continuation of U.S. patent application Ser. No. 993,848 filed Dec. 18, 1997, pending.

FIELD OF THE INVENTION

The present invention relates to the use of steroid compounds substituted in position 11 for the production of medicaments intended for replacement hormone treatment for the menopause having only little or no estrogen activity at the uterine level.

STATE OF THE ART

Osteoporosis is a pathology which is characterized by a quantitative and qualitative reduction in bone matter, sufficient to lead to vertebral or peripheral fractures, in a spontaneous fashion or, on occasions, due to minimal traumas. Although this illness has many factors at its origin, it is the menopause, which in woman, constitutes the dominating factor in bone loss or osteopenia.

This osteopenia manifests itself by a rarefaction and a modification of the architecture of the spongy bone, the consequence of which is to increase the fragility of the skeleton and the risk of fractures. Bone loss increases strongly after menopause due to the suppression of ovarian function and reaches 3 to 5% per year before slowing down after 65 years of age.

For a therapeutic purpose, the post-menopause hormonal deficiency can be compensated for by a hormone replacement therapy where estrogen plays a major role in preserving the bone mass. But long-term estrogenotherapy is sometimes accompanied by undesirable effects on the genital apparatus (endometrial hyperplasia, breast tumors . . . ), which constitutes a major drawback and limits its use.

OBJECTS OF THE INVENTION

It is an object of the invention to provide a method of treating menopause or perimenopause in women with compounds other than estradiol having a dissociated estrogen activity, namely an estrogen activity at the bone level, while having none or little of the endometrial hyperplasia activity, nor breast tumor proliferation activity.

This and other objects and advantages of the invention will become obvious from the following detailed description.

THE INVENTION

The novel method of the invention for treating menopause or perimenopause without estrogenic activity at the uterine level in women comprises administering to women an amount of a steroid of the formula

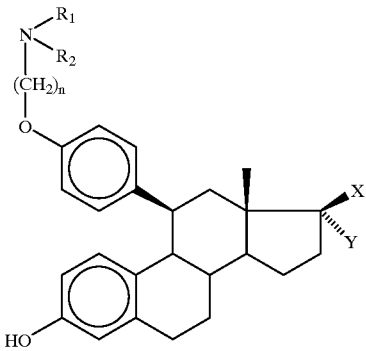

wherein n is 2 or 3, $R_1$ and $R_2$ are individually selected from the group consisting of hydrogen and alkyl of 1 to 4 carbon atoms or taken together with the nitrogen atom to which they are attached form aromatic or non-aromatic, saturated or unsaturated, mono or polycyclic heterocycles of 5 to 15 ring members optionally containing in the ring up to 3 heteroatoms selected from the group consisting of oxygen, sulfur and optionally substituted nitrogen, X is optionally esterified hydroxy and Y is selected from the group consisting of hydrogen and alkenyl and alkynyl of 2 to 4 carbon atoms or X and Y form =O or X and Y together with the carbon atom to which they are attached form a member selected from the group consisting of

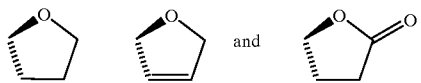

and their non-toxic, pharmaceutically acceptable acid addition salts sufficient to treat menopause or perimenopause symptoms without estrogenic activity at the uterine level.

Examples of alkyl of 1 to 4 carbon atoms are methyl, ethyl, propyl, isopropyl, n-butyl, isobutyl and tert-butyl.

Examples of $R_1$ and $R_2$ together with the nitrogen atom are mono and bicyclic heterocycles such as pyrrolyl, imidazolyl, indolyl, pyridyl, pyrazinyl, pyrimidinyl, pyridazinyl, thiazolyl, oxazolyl, furazonyl, pyrazolinyl, thiazolinyl, and particularly the following saturated heterocycles:

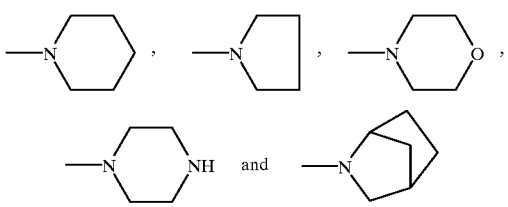

When the heterocycle is substituted, it is particularly by an alkyl of 1 to 4 carbon atoms on the nitrogen atom.

Examples of alkenyl and alkynyl of 2 to 4 carbon atoms are —C≡CH, —C≡C—Me, —C≡C—CH$_2$CH$_3$, —CH=CH$_2$, —CH=CH~Me, —CH=CH~CH$_2$CH$_3$. The wavy line indicates that the alkenyl has an (E) or (Z) configuration.

Examples of optionally esterified hydroxy are

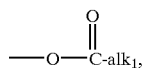

wherein $alk_1$ is alkyl of 1 to 4 carbon atoms, preferably methyl or ethyl.

Examples of organic and inorganic acids for the preparation of non-toxic, pharmaceutically acceptable acid addition salts are hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane or ethane sulfonic acid, arylsulfonic acids such as benzene or paratoluene sulfonic acid and arylcarboxylic acids.

Among the symptoms and consequences of menopause are more precisely hot flushes, sweats, vaginal atrophy and dryness, urinary symptoms and in the long term, a reduction in bone density and an increased risk of fractures, as well as the loss of the cardiovascular protection offered by the estrogens.

Therefore, a more particular subject of the invention, is a method for the prevention or the treatment of osteoporosis having only little or no estrogen activity at the uterine level which comprises administering to women an amount of the steroid of formula (I).

Among the preferred compounds of Formula I are those wherein n is 2, those wherein $R_1$ and $R_2$ are individually alkyl of 1 to 4 carbon atoms, those wherein $R_1$ and $R_2$ together with the nitrogen form piperidino, pyrrolidino or 2-aza-bicyclo (2,2,1)hept-2-yl, those wherein X is —OH and Y is hydrogen, —C≡CH, —C≡C—$CH_3$, —CH=CH~$CH_3$ or (Z)—CH=CH~$CH_3$ and those wherein X and Y together with the carbon atom form one of the above rings and their salts.

Examples of specific steroids are

11β-[4-[2-(dimethylamino)ethoxyl]phenyl]-19-nor-17αΔ1, 3,5(10)-pregnatrien-20-yn-3,17β-diol, 11β-[4-[1-pyrrolidinyl)ethyoxy]phenyl]-Δ1,3,5(10)-estratrien-3,17β-diol, 11β-[4-[2-(1-piperidinyl)ethoxy]phenyl]-Δ1,3,5(10)-estratrien-3, 17β-diol, (17R) 11β-[4-[2-(dimethylamino)ethoxy]phenyl]-spiro-(Δ1,3,5(10)-estratrien-17,2'(5'H)-furan)-3-ol, (17R) 4',5'-dihydro-11β-[4-[2-(dimethylamino)ethoxy] phenyl]-spiro(Δ',3,5,(10)-estratien-17,2'(3'H)-furan)-3-ol, 11β-[4-[2-(diethylamino)ethoxy]phenyl]-19-nor-17α-Δ1,3, 5(10)-pregnatrien-20-yn-3,17β-diol, 11β-[4-[1-diethylamino)ethoxy]phenyl]-Δ1,3,5(10)-estratrien-3,17β-diol, 11β-[4-[2-(1-piperidinyl)ethoxy]phenyl]-19-nor-17α-Δ1,3, 5(10)-pregnatrien-20-yn-3,17β-diol, gamma-lactone of (17α)-11β-[4-[2-(diethylamino)ethoxy] phenyl]-3,17β-dihydroxy-19-nor-Δ1,3,5(10)-pregnatriene-21-carboxylic acid, gamma-lactone of (17α)-3,17β-dihydroxy-11β-[4-[2-(1-piperidinyl)ethoxy]phenyl]-19-nor-Δ1,3,5(10)-pregnatriene-21-carboxylic acid, 11β-[4-[2-(diethylamino)ethoxy]phenyl]-Δ1,3,5,(10)-estratrien-3-ol-17-one, 11β-[4-[2-(1-piperidinyl)ethoxy]phenyl]-Δ1,3,5(10)-estratrien-3-ol-17-one and 11β-[4-[2-(2-aza-bicyclo(2.2.1.)hept-2-yl)ethoxy]phenyl]-Δ1,3,5(10)-estratrien-3,17β-diol.

The compounds of formula I are known and are generally described in the following patents: EP-B-0097572, FR-B-2640977, EP-B-0305242, FR-B-2596395, EP-B-0308345. In these patents, the compounds are taught as having an antiglucocorticoid, antiprogestomimetic, progestomimetic, androgenic, antiandrogenic, estrogenic or antiestrogenic activity.

Applicant has found new properties concerning a very restricted selection of these compounds having as common point, in position 11, an optionally substituted aminoalkyloxy and the aromatic ring A is substituted by an 3-hydroxy.

In fact, it is no case taught in these patents that the products of formula (I) of the invention have a dissociated estrogenic activity. By dissociated estrogenic activity is meant an estrogenic activity at the bone level while demonstrating only a minimal activity at the uterine level, thus not entailing endometrial proliferation, an activity which is much lower than that of estradiol.

Furthermore, the compounds of the invention have the following advantages: They have an anti-estrogen activity at the level of the breast. As opposed to estradiol, they do not stimulate the growth of human mammary tumor cells and can even inhibit their growth. The compounds of the invention are therefore particularly advantageous for the treatment of menopause in women at risk from breast cancer (family antecedents) who are therefore excluded from a replacement treatment using estradiol.

They lead to a lowering of the seric cholesterol to a level equal to that induced by estradiol and therefore they strengthen cardiovascular protection. Finally, the compounds of the invention do not have an estrogenic activity at the uterine level, which does not require them to be administered in combination with a progestomimetic compound.

The compounds of formula (I) are administered digestive, parenterally or locally, for example by percutaneous route. They can be in the form of plain or coated tablets, capsules, granules, suppositories, ovules, injectable preparations, ointments, creams, gels, microspheres, implants, intravaginal rings, patches and sprays, which are prepared according to usual methods.

The active ingredient or ingredients can be incorporated with the excipients usually employed in these pharmaceutical compositions such as talc, gum arabic, lactose, starch, magnesium stearate, cocoa, aqueous or non-aqueous vehicles, fatty substances of animal or vegetable origin, paraffin derivatives, glycols, various wetting, dispersing or emulsifying agents, preservatives.

The useful dose varies as a function of the illness to be treated and the administration route. It can vary for example from 0.0075 to 1.5 mg/kg per day for an adult by oral route.

Certain compounds of formula I are compounds known solely as intermediate compounds such as the compounds of formula I in which $R_1$ and $R_2$ individually are alkyl of 1 to 4 carbon atoms and X and Y form together an oxo, as well as their addition salts with pharmaceutically acceptable acids.

In the following examples, there are described several preferred embodiments to illustrate the invention. However, it is to be understood that the invention is not intended to be limited to the specific embodiments.

Pharmacological tests

Molecules studied

E2: estradiol

A: 11β-[4-[2-(1-pyrrolidinyl)ethoxy]phenyl]-Δ1,3,5(10)-estratriene-3,17β-diol,

B: 11β-[4-[2-(1-piperidinyl)ethoxy]phenyl]-Δ1,3,5,(10)-estratriene-3,17β-diol,

C: 11β-[4-[2-diethylamino)ethoxy]phenyl]-Δ1,3,5(10)-estratriene-3,17β-diol,

D: 11β-[4-[2-(1-piperidinyl)ethoxy]phenyl]-19-nor-17α-Δ1,3,5(10)-pregnatrien-20-yn-3,17β-diol, E: 11β-[4-[2-(1-piperidinyl)ethoxy]phenyl]-Δ1,3,(10)-estratrien-3-ol-17-one.

Effect on the proliferation of mammary cells

The proliferative activity of the molecules was studied in comparison to that of estradiol on MCF-7 human mammary cells in culture. To reveal an agonist effect of estradiol and/or the tested molecules, the cell maintenance culture (rich in growth factors and steroids) was replaced by an impoverished medium, among others free of steroids (DMEM supplemented with 5% of steroid-free serum and without phenol red). Cells underwent this severance two days before the start of the test.

After 7 days culture in the presence of the products to be studied, the cell proliferation was evaluated by determination of the DNA. In each test, the effect of estradiol at $10^{-10}$M (cell growth in the presence of estradiol less cell growth in the presence of the solvent) determined the 100% agonist activity. The activity of the molecules was evaluated in comparison to this internal control. The molecules inducing an identical cell growth to that observed with the solvent alone were classified as "inactive" with those inducing a lower cell growth to that observed with the solvent were classified as "inhibitor".

|          | E2      | A        | B        | D         |
|----------|---------|----------|----------|-----------|
| Activity | Agonist | inactive | inactive | inhibitor |

Study of the bone impact of a product in female rats ovariectomized at the age of 3 months.

Compounds A, B, C, D, E were tested to determine their effect on bone mass and on formation and resorption activity in the model of the ovariectomized rat at the age of 3 months. The animals were treated in a preventive fashion.

| Animals: | |
|---|---|
| Species | Rat |
| Strain | Sprague-Dawley |
| Sex | Female |
| Weight | 250 g to 280 g |
| No. of animals/group | 8 |

Products:
1—Product to be tested: Products A, B, C, D, E
vehicle(s): corn oil, 0.5% methylcellulose,
dose(s): one dose per tested product (0.3 mg/kg/d)
number of administrations: once/day; 5 days/week for 4 weeks
administration route: orally for the products
volumes: 5 ml/kg (p.o.)
period between the last injection and sacrifice: 24 hours
number of administrations: 20.
2—Reference product: 17β-estradiol was administered subcutaneously at a dose of 0.1 mg/kg/d in solution in a mixture of corn oil-benzyl alcohol (99:1, v/v) under a volume of 0.2 ml/kg.

Experimental protocol

Animals

The study was carried out with female rats ovariectomized at the age of 3 months and the animals were kept in an air conditioned room (temperature 20° C.±2° C.) and grouped by 4 into boxes. The animals received ad libitum, demineralized water and compressed foods (pellets: A04CR-10 UAR).

Surgery

The 3 month old female rats weighing approximately 250 g were ovariectomized under anesthesia with Imalgene 1000, at a dose of 100 mg/kg by intraperitoneal route (i.p.) and under a volume of 1 ml/kg. They also received Nembutal (3 mg/kg i.p. under a volume of 0.3 ml/kg). After lateral incision, cutaneous and muscular planes were sectioned. The exeresis of each ovary was carried out after ligature of the oviduct. The "SHAM" control rats were anesthetized under the same conditions. After incision of the cutaneous and muscular planes, each ovary was exposed, then replaced in situ.

Treatment

The effects of the products were determined in a preventive treatment and they were administered immediately after the ovariectomy. The animals were distributed into groups of 8.

Group 1: "SHAM" control rats receiving the vehicle or vehicles

Group 2: "OVX" control rats receiving the vehicle or vehicles

Group X: "OVX" rats receiving respectively defined doses of the product or products to be tested.

Blood samples

At the end of 4 weeks (duration of the study), the animals were decapitated by guillotine and the serums collected after centrifugation were preserved at −20° C.

A lipidic balance was established from the serous determinations of total cholesterol, of triglycerides and of phospholipids on a 500 μl aliquot of serum. The lowering of the seric cholesterol level was expressed in % relative to the level shown by the ovariectomized animals receiving only the solvent.

Organ samples

After sacrificing the animals, the following organs were removed:

tractus genitalis

The uteri were removed and the latter were weighed. The increase in weight was expressed in % of the weight of the uterus of ovariectomized animals receiving only the solvent.

at bone level:

The bone mass (BMD or Bone mineral density) was measured by biphotonic dual energy X-ray absorptiometry (DEXA). The measurements were carried out on bone excized and cleaned of all soft tissue. The BMD (Bone mineral density) was measured on the whole bone as well as on the metaphyseal part at the level of the proximal extremity for the left tibia. This zone was defined as being the region which is richest in trabecular bone; and consequently, was the most sensitive to variations in bone volume and bone mineral density.

The results are expressed in % according to the formula:

$$\frac{\text{Tested product } BMD - OVX\ BMD}{\text{SHAM } BMD - OVX\ BMD} \times 100$$

|    | Dose mg/kg | TIBIA BONE density % | UTERUS Weight % | Cholesterol % |
|----|------------|----------------------|-----------------|---------------|
| E2 | 0.1 sc     | 105                  | 359             | −35           |
| A  | 0.3 po     | 68                   | 70              | −53           |
| B  | 0.3 po     | 60                   | 68              | −50           |
| C  | 0.3 po     | 63                   | 75              | −55           |
| D  | 0.3 po     | 66                   | 88              | −50           |

| | Dose mg/kg | TIBIA BONE density % | UTERUS Weight % | Cholesterol % |
|---|---|---|---|---|
| E | 0.3 po | 77 | 59 | −52 |
| OVX | | 0 | | |
| SHAM | | 100 | | |

Note: For estradiol: average of 4 tests, for compound B, average of 3 tests.

Conclusion

The compounds of the invention offer an effective bone protection (>60%), while showing a minimal uterotropic activity compared to that caused by estradiol. Moreover, a significant decline in total cholesterol level was observed.

Various modifications of the method of the invention may be made without departing from the spirit or scope thereof and it should be understood that the invention is intended to be limited only as defined in the appended claims.

What is claimed is:

1. A method of treating menopause or perimenopause without estrogenic activity at the uterine level in women comprising administering to women an amount of a steroid of the formula

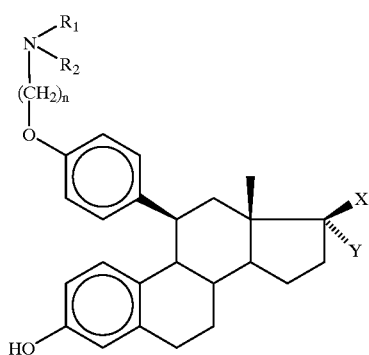

wherein n is 2 or 3, $R_1$ and $R_2$ are individually selected from the group consisting of hydrogen and alkyl of 1 to 4 carbon atoms or taken together with the nitrogen atom to which they are attached form aromatic or non-aromatic, saturated or unsaturated, mono or polycyclic heterocycles of 5 to 15 ring members optionally containing in the ring up to 3 heteroatoms selected from the group consisting of oxygen, sulfur and optionally substituted nitrogen, X is optionally esterified hydroxy and Y is selected from the group consisting of hydrogen and alkenyl and alkynyl of 2 to 4 carbon atoms or X and Y form =O or X and Y together with the carbon atom to which they are attached form a member selected from the group consisting of

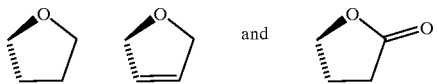

and their non-toxic, pharmaceutically acceptable acid addition salts sufficient to treat menopause or perimenopause symptoms without estrogenic activity at the uterine level.

2. The method of claim 1 for preventing or treating osteoporosis.

3. The method of claim 1 wherein n is 2.

4. The method of claim 3 wherein X is —OH and Y is selected from the group consisting of hydrogen, —C≡—CH, —C≡C—$CH_3$, (E) —CH=CH~$CH_3$ and (Z) —CH=CH~$CH_3$ or X and Y together with the carbon form a ring and $R_1$ and $R_2$ are individually alkyl of 1 to 4 carbon atoms or taken with the nitrogen form a member of the group consisting of piperidino, pyrrolidino and 2-bicyclo (2,2,1) hept-2-yl.

5. The method of claim 1 wherein the compound is selected from the group consisting of 11β-[4-[2-(dimethylamino)ethoxyl]phenyl]-19-nor-17αΔ1,3,5(10)-pregnatrien-20-yn-3,17β-diol, 11β-[4-[1-pyrrolidinyl)ethyoxy]phenyl]-Δ1,3,5(10)-estratrien-3,17β-diol, 11β-[4-[2-(1-piperidinyl)ethoxy]phenyl]-Δ1,3,5(10)-estratrien-3, 17β-diol, (17R) 11β-[4-[2-(dimethylamino)ethoxy]phenyl]-spiro-(Δ1,3,5(10)-estratrien-17,2'(5'H)-furan)-3-ol, (17R) 4',5'-dihydro-11β-[4-[2-(dimethylamino)ethoxy]phenyl]-spiro(Δ',3,5,(10)-estratien-17,2'(3'H)-furan)-3-ol, 11β-[4-[2-(diethylamino)ethoxy]phenyl]-19-nor-17α-Δ1,3,5(10)-pregnatrien-20-yn-3,17β-diol, 11β-[4-[1-diethylamino)ethoxy]phenyl]-Δ1,3,5(10)-estratrien-3,17β-diol, 11β-[4-[2-(1-piperidinyl)ethoxy]phenyl]-19-nor-17α-Δ1,3,5(10)-pregnatrien-20-yn-3,17β-diol, gamma-lactone of (17α)-11β-[4-[2-(diethylamino)ethoxy]phenyl]-3,17β-dihydroxy-19-nor-Δ1,3,5(10)-pregnatriene-21-carboxylic acid, gamma-lactone of (17α)-3,17β-dihydroxy-11β-[4-[2-(1-piperidinyl)ethoxy]phenyl]-19-nor-Δ1,3,5(10)-pregnatriene-21-carboxylic acid, 11β-[4-[2-(diethylamino)ethoxy]phenyl]-Δ1,3,5,(10)-estratrien-3-ol-17-one, 11β-[4-[2-(1-piperidinyl)ethoxy]phenyl]-Δ1,3,5(10)-estratrien-3-ol-17-one and 11β-[4-[2-(2-aza-bicyclo(2.2.1.)hept-2-yl)ethoxy]phenyl]-Δ1,3,5(10)-estratrien-3,17β-diol.

6. The method of claim 3 wherein $R_1$ and $R_2$ are individually alkyl of 1 to 4 carbon atoms and X and Y are =0.

7. The method of claim 1 wherein the women treated are at risk from breast cancer.

* * * * *